United States Patent [19]

Bearda

[11] 4,250,391
[45] Feb. 10, 1981

[54] APPARATUS FOR STERILIZING LIQUIDS

[75] Inventor: Pieter Bearda, Turgi, Switzerland

[73] Assignee: BBC Brown Boveri & Company Limited, Baden, Switzerland

[21] Appl. No.: 42,526

[22] Filed: May 25, 1979

[30] Foreign Application Priority Data

Jun. 7, 1978 [CH] Switzerland .................... 6207/78

[51] Int. Cl.³ .................... G01M 21/24; G01J 1/00
[52] U.S. Cl. .................... 250/504 R; 250/436
[58] Field of Search ............. 250/504, 436, 437, 438

[56] References Cited

U.S. PATENT DOCUMENTS

| 2,243,632 | 5/1941 | Johnson | 250/436 |
| 3,637,342 | 1/1972 | Veloz | 250/436 |
| 3,792,230 | 2/1974 | Ray | 250/504 |

*Primary Examiner*—Harold A. Dixon
*Attorney, Agent, or Firm*—Oblon, Fisher, Spivak, McClelland & Maier

[57] ABSTRACT

The invention relates to an apparatus for sterilizing liquids by means of ultraviolet rays, using as the radiation source a low pressure, high current, mercury vapor lamp (UV lamp) which is provided with an appendix-shaped piece of tube (appendix) located on the discharge tube. In order to be able to regulate the temperature of the appendix in a defined manner even while the lamp is in operation and in order to achieve longer life of the UV lamp, an airstream circulating through the apparatus is used to cool the UV lamp. This airstream follows a path such that the air warmed on the discharge tube travels past the electrode bulbs of the UV lamp to the outer wall of the pipeline, through which pipeline the liquid to be sterilized flows. The air which has cooled on the outer wall of the pipeline is then returned to the UV lamp and must be at a temperature which is lower than the operating temperature of the appendix, so that the temperature of the latter can be regulated in a defined manner by means of a heater.

5 Claims, 1 Drawing Figure

U.S. Patent  Feb. 10, 1981  4,250,391
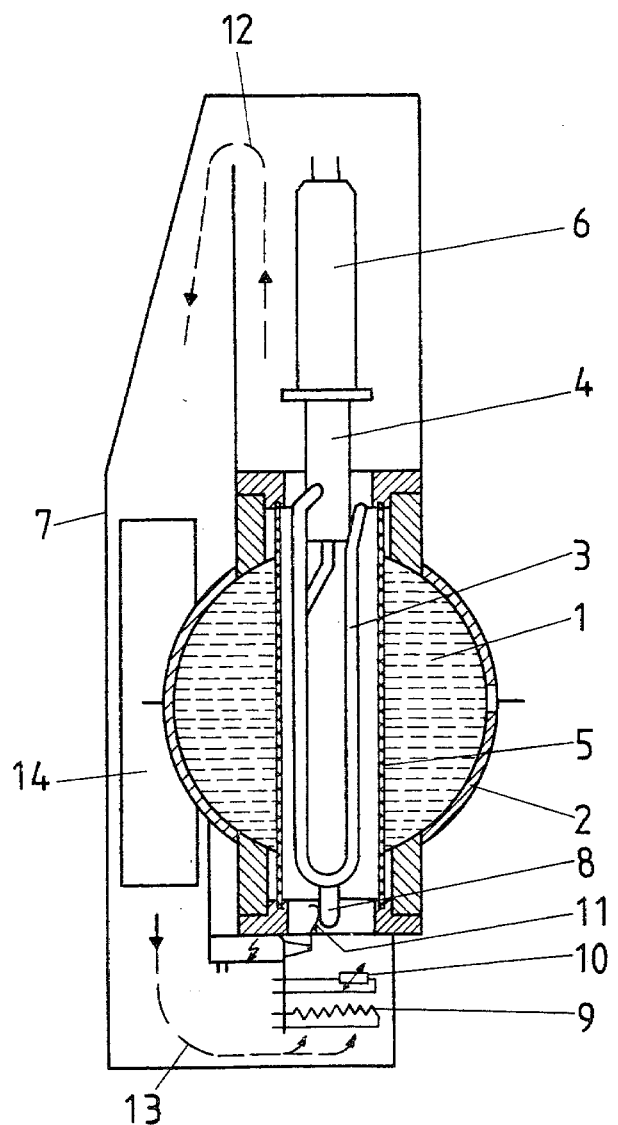

APPARATUS FOR STERILIZING LIQUIDS

BACKGROUND OF THE INVENTION

1. Field of the Invention

The invention relates to an apparatus for sterilizing liquids by means of ultraviolet rays, wherein the radiation source used is a low pressure, high current, mercury vapour lamp (UV lamp) which is provided with an appendix-shaped piece of tube (appendix) located on the discharge tube.

2. Description of the Prior Art

Apparatus for sterilizing liquids, which utilize ultraviolet radiation sources, are disclosed, for example, in German Offenlengungsschrift No. 2,630,496 and U.S. Pat. No. 3,637,342. In cases where the discharge tube of the UV lamp possessed an appendix for creating the mercury vapour pressure, the space in which the UV lamp was fixed was, in the previously used apparatus, divided essentially into three thermally mutually separate chambers, namely a bottom chamber, in which was located the "appendix" of the UV lamp, a middle chamber, in which was located the discharge space of the lamp, and a round chamber in which the liquid to be sterilized flowed, and an upper part which accommodated the electrode bulbs and which was cooled by cooling fins. The three-chamber division appeared necessary so that on the one hand the operating temperature of the discharge zone (as a rule $\geq 300°$ C.) did not excessively heat the appendix which, being the coldest point (as a rule $\leq 65°$ C.) of the system, is responsible for the mercury vapour pressure and hence also for the radiation intensity, while on the other hand the upper space was also not excessively heated by the discharge zone, since this space, which is accessible from the exterior, was, for safety reasons, not allowed to become excessively hot.

In order that the UV lamp should be able to "strike" at all, the entire appendix section had to be preheated by means of a resistance heater before striking the lamp. On switching on the anode current, this heating was again switched off. In operation, the temperature of the appendix was determined by the heat fed back from the discharge zone, and by the temperature of the surrounding air. This in turn varied with the water temperature. The temperature of the appendix therefore had to be corrected, depending on the time of year, by using suitable spacers by means of which the appendix was lowered to a greater or lesser degree into the bottom chamber.

The previous apparatus suffered from the disadvantage that on heating the appendix in order to strike the lamp, the middle part, and hence the discharge zone, remained cold. Hence, the mercury was able to recondense there, which made it more difficult for the lamp to strike. On the other hand, the high temperature of the discharge zone in the middle chamber during operation was extremely detrimental to the life of the UV lamp.

SUMMARY OF THE INVENTION

It is the object of the present invention to provide an apparatus of the initially mentioned type in which the temperature of the appendix can be regulated in a defined manner even during operation of the lamp, and which is of simple construction and ensures a longer life of the UV lamp than was the case with the apparatus hitherto employed.

BRIEF DESCRIPTION OF THE DRAWING

Various objects, features and attendant advantages of the present invention will be more fully appreciated as the same becomes better understood from the following detailed description when considered in connection with the accompanying drawing and wherein:

The sole FIGURE shows schematically the cross-section of a sterilizing apparatus according to the invention.

DETAILED DESCRIPTION OF THE PREFERRED EMBODIMENT

The medium 1 which is to be sterilized flows through a pipeline 2 in which, for example, a U-shaped discharge tube 3 of the UV lamp 4 is located in a quartz protective tube 5. The UV lamp 4 is located in a housing H defining a continuous space which is not subdivided into chambers. The upper part of this space, in which the electrode bulbs 6 are located, is above the pipeline 2 and is connected by means of a tube 7 to the lower part of the space, in which are present the appendix 8 and the heater 9 (as is known in the art, the appendix 8 comprises a collection chamber for mercury condensed in the discharge tube 3). The connecting tube 7 is in thermal contact with the flowing medium 1. The heater 9 is controlled by a regulator which keeps the temperature at the appendix 8 at a constant level by means of a temperature sensor 10. Reference numeral 11 marks a high voltage, high frequency, initiating electrode located at the appendix 8, by means of which the UV lamp 4 is struck.

The mode of action of this apparatus is based on the fact that the air 12 warmed by the heater and by the discharge rises upwards, passes into the connecting tube 7 and is there cooled in contact with the pipeline 2 on which, where appropriate, additional metal cooling fins 14 can be provided, after which the cooled air 13 again comes into contact with the UV lamp. When it does so, it is the space around the appendix 8 which is first cooled. The number of cooling fins and their size, as well as the dimensions of the surface of the pipeline 2 which comes into contact with the air 12 which is to be cooled, are selected so that the airstream 13 is at a temperature below the operating temperature of the appendix 8. The predetermined temperature of the appendix is then set by means of the heater 9, which in turn is regulated via the sensor 10.

If the apparatus is operated in the manner shown in the sole FIGURE, that is to say if the electrode bulbs 6 of the UV lamp 4 point upwards and the appendix 8 points downwards, air circulation takes place by convection alone. Additional measures, such as the introduction of air circulating pump or of a fan, are not necessary.

Although the appendix 8 directly adjoins the discharge tube 3, defined appendix temperatures of $\leq 65°$ C. can be obtained in the apparatus described even with operating temperatures of the discharge tube 3 of $\geq 300°$ C.

A further advantage of the novel apparatus is that the discharge tube 3 is prewarmed during striking which facilitates the striking process. Furthermore, the operating temperature of the discharge tube is reduced which increases the life of the UV lamp. In addition, when using the UV lamp, the appendix no longer has to be introduced in a controlled manner into the orifice present, as in the previously used apparatuses, in the partition inserted between the bottom and middle chambers. Finally, the appendix remains freely accessible for the initiating electrode and there is no collision with the heater which heater must not interact with the initiating electrode.

Obviously numerous modifications and variations of the present invention are possible in ligth of the above teachings. It is therefore to be understood that within the scope of the appended claims, the invention may be practiced otherwise than as specifically described herein.

What is claimed as new and desired to be secured by Letters Patent of the United States is:

1. An apparatus for sterilizing liquids by means of ultraviolet rays, wherein the source of radiation used is a low pressure, high current, mercury vapour lamp having a discharge tube on which is located an appendix-shaped piece of tube defining a mercury collecting chamber for collecting mercury condensed in the discharge tube, comprising:
   a pipeline through which said liquids to be sterilized flow;
   a housing attached to said pipeline, including a part transparent to ultraviolet rays extending transversely through the pipeline and a part in communication with the outer wall of the pipeline, said parts being in fluid communication with one another and defining a fluid circulating path, for circulation of fluid through the housing;
   the discharge tube of the lamp being disposed in the part transparent to ultraviolet rays whereby ultraviolet rays from the discharge tube sterilize the liquid flowing through the pipeline;
   heater means in the housing for heating fluid circulating through the housing; and
   means for circulating a stream of air through the housing such that the air which has become warmed on the discharge tube travels through the housing and to the connecting part in communication with an outer wall of the pipeline, the air being cooled on the outer wall of the pipeline and being returned to the lamp at a temperature lower than the operating temperature of the appendix-shaped piece of tube, and the air first reaching the appendix-shaped piece of tube, wherein a predetermined temperature of the appendix-shaped piece of tube is regulated by air flowing over it and heated by said heater means, to thereby prolong the life of the lamp and also facilitate start up of the lamp.

2. An apparatus according to claim 1, wherein the housing has an upper part, a lower part and a connecting part between the upper and lower parts, said connecting part being the part in communication with the outer wall of the pipeline, and the part transparent to ultraviolet rays being connected between the upper and lower parts.

3. An apparatus according to claim 2, wherein said lamp has at least one electrode bulb, said electrode bulb being disposed in the upper part of the housing, and the appendix-shaped piece of tube being in the lower part of the housing.

4. An apparatus according to claim 3, wherein at least one metal cooling fin is fixed to the outer wall of the pipeline and is disposed in the connecting part of the housing.

5. An apparatus according to claim 1 or 2 or 3 or 4, wherein a temperature sensor is disposed in the lower part of the housing upstream of the appendix-shaped piece of tube and downstream of the heater means, relative to the direction of circulation of air through the housing, to regulate the heater and maintain proper temperature of air flowing over the appendix-shaped piece of tube.

* * * * *